United States Patent

[19] Ramin et al.

[11] Patent Number: 6,110,447
[45] Date of Patent: Aug. 29, 2000

[54] COSMETIC COMPOSITIONS COMPRISING A FILM-FORMING POLYMER A CITRIC ACID ESTER AND A PLASTICIZING AGENT

[75] Inventors: Roland Ramin, Paris; Philippe Gabin, Bures sur Yvette, both of France; Chris Frankfurt, Bridge, N.J.

[73] Assignee: L'Oreal, Paris, France

[21] Appl. No.: 09/023,718

[22] Filed: Feb. 13, 1998

[30] Foreign Application Priority Data

Jul. 1, 1997 [FR] France ................... 97 08281

[51] Int. Cl.[7] ............... A61K 7/42; A61K 7/04; A61K 7/06
[52] U.S. Cl. ................ 424/61; 424/59; 424/70.1
[58] Field of Search ............. 424/61, 59, 70.1

[56] References Cited

U.S. PATENT DOCUMENTS

| | | |
|---|---|---|
| 4,740,370 | 4/1988 | Faryniarz et al. . |
| 4,749,564 | 6/1988 | Faryniarz et al. . |
| 4,822,423 | 4/1989 | Soyama et al. . |
| 5,100,944 | 3/1992 | Walker et al. . |
| 5,145,670 | 9/1992 | Castrogiovanni et al. . |
| 5,145,671 | 9/1992 | Castrogiovanni et al. . |
| 5,225,185 | 7/1993 | Castrogiovanni et al. . |
| 5,227,155 | 7/1993 | Castrogiovanni et al. . |

FOREIGN PATENT DOCUMENTS

| | | |
|---|---|---|
| 2151654 | 4/1973 | France . |
| 54138134 | 10/1979 | Japan ......................... 424/61 |
| 1225544 | 3/1971 | United Kingdom . |

*Primary Examiner*—Thurman K. Page
*Assistant Examiner*—Susan Tran
*Attorney, Agent, or Firm*—Finnegan, Henderson, Farabow, Garrett & Dunner, L.L.P.

[57] ABSTRACT

A composition comprising a combination of:

(a) at least one film-forming polymer;

(b) at least one citric acid ester of formula (I):

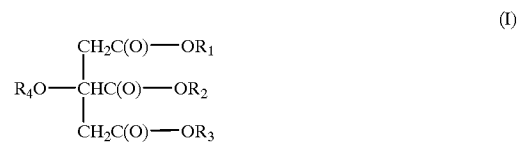

in which:

$R_1$, $R_2$ and $R_3$ independently represent H or a saturated or unsaturated, linear or branched $C_1$–$C_{30}$ alkyl chain or a saturated or unsaturated cyclic $C_3$–$C_{30}$ alkyl chain, wherein at least one of $R_1$, $R_2$ and $R_3$ is not a hydrogen atom, $R_4$ represents a hydrogen atom or an $R'_4$—CO— group in which $R'_4$ represents a saturated or unsaturated, linear or branched $C_1$–$C_8$ alkyl group or a saturated or unsaturated cyclic $C_3$–$C_8$ alkyl group; and (c) at least one compound of formula (II):

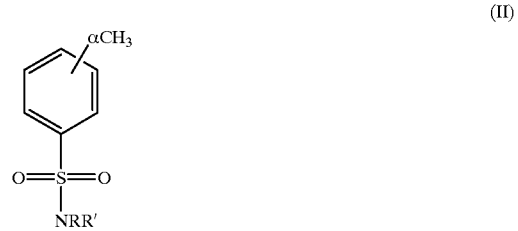

in which $\alpha$ represents an ortho or para position of the phenyl group, and R and R' independently represent a hydrogen atom or a $C_1$–$C_6$ alkyl group, and cosmetic and/or dermatological compositions comprising such a combination.

27 Claims, No Drawings

COSMETIC COMPOSITIONS COMPRISING A FILM-FORMING POLYMER A CITRIC ACID ESTER AND A PLASTICIZING AGENT

The present invention relates to novel cosmetic compositions. More particularly, the invention relates to cosmetic and care compositions comprising at least one film-forming polymer. These novel compositions exhibit improved properties with respect to the prior art, in particular with regard to the fluidity of the composition, the ease of application, the homogeneity of the film, the speed of drying, the resistance of the film to wear, the gloss, the resistance to yellowing, the stability to light and the stability to heat.

Film-forming polymers are essential constituents of numerous cosmetic forms, such as, for example, nail varnishes, lacquers and mascaras. They make it possible to deposit the make-up in the form of a film on the surface of the skin, the hair and/or the nails. Normally, at least one so-called plasticizing compound is added to the film-forming polymer, the role of this plasticizing compound being to confer flexibility on the make-up film. This is because the use of a film-forming polymer alone gives a stiff, brittle and fragile film which rapidly wears away. However, the addition of a plasticize can sometimes lead to other disadvantages, such as yellowing, instability of the composition towards light and/or towards heat, lack of gloss or lack of fluidity.

Indeed, nail varnish compositions comprising N-ethyl-o,p-toluenesulphonamiid (mixture of the ortho and para isomers) as the plasticizing agent, in combination with film-forming polymer, are known, in particular from European Patent Application EP-154,679. However, such a combination exhibits the disadvantage of rapidly yellowing and of being unstable when it is exposed to light and/or to heat.

The use of a citrate, such as, for example, tributyl acetylcitrate, as a plasticizing agent in combination with a film-forming polymer is also known. To this end, reference may be made to U.S. Pat. No. 5,227,155. However, such compositions lack gloss and fluidity and are difficult to apply.

The present invention is targeted at providing a make-up composition exhibiting improved properties with respect to the prior art.

The inventors have discovered, surprisingly, that the combination of a film-forming polymer with an ester of citric acid corresponding to the formula (I) (hereinbelow) and of a plasticizing compound of formula (II) (hereinbelow) makes it possible to overcome the disadvantages of the prior art.

The present invention relates to a novel composition comprising the combination of:

(a) at least one film-forming polymer;
(b) at least one citric acid ester of formula (I):

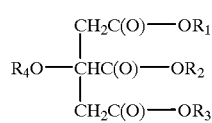

in which:

$R_1$, $R_2$ and $R_3$ independently represent H or a saturated or unsaturated, linear or branched $C_1$–$C_{30}$ alkyl chain or a saturated or unsaturated cyclic $C_3$–$C_{30}$ alkyl chain, wherein at least one of $R_1$, $R_2$ and $R_3$ is not a hydrogen atom, and $R_4$ represents a hydrogen atom or an $R'_4$—CO— group in which $R'_4$ represents a saturated or unsaturated, linear or branched $C_1$–$C_8$ alkyl group or a saturated or unsaturated cyclic $C_3$–$C_8$ alkyl group; and (c) at least one compound of formula (II):

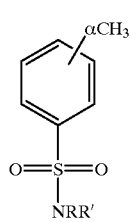

in which:

α represents an ortho or para position of the phenyl group and R and R' independently represent a hydrogen atom or a saturated or unsaturated, linear or branched $C_1$–$C_6$ alkyl group or a saturated or unsaturated cyclic $C_3$–$C_6$ alkyl group.

The combination according to the invention, when it is incorporated in a cosmetically acceptable vehicle, spreads over the skin, mucous membranes, eyelashes, eyebrows, hair or nails with great ease and makes it possible to obtain a homogeneous film which rapidly dries and which exhibits improved resistance and improved gloss with respect to the compositions of the prior art. Such a composition withstands yellowing and is stable towards light and towards heat.

The film-forming polymers that can be used in accordance with the present invention can be selected from:

keratin derivatives, such as keratin hydrolysates and sulphonic keratins;

anionic, cationic, amphoteric or non-ionic chitosan or chitin derivatives;

cellulose derivatives, such as hydroxyethylcellulose, hydroxypropylcellulose, methylcellulose, ethylhydroxyethylcellulose or carboxymethylcellulose, as well as quaternized cellulose derivatives; mention may in particular be made of nitrocelluloses of the "RS" or "SS" type and in particular nitrocellulose type ¼"RE", nitrocellulose type ½"RS", nitrocellulose type ½"SS" and nitrocellulose type ¾"RS";

acrylic polymers or copolymers, such as polyacrylates or polymethacrylates;

resins of the acrylic, styrene, acrylate-styrene and vinyl type;

polyvinylpyrrolidones and vinyl copolymers, such as copolymers of methyl vinyl ether and of maleic anhydride or the copolymer of vinyl acetate and of crotonic acid;

polyester polymers, alkyd resins and/or anionic polyester amides which are dispersible in water comprising monomers carrying an —$SO_3M$ functional group, with M representing a hydrogen atom, an ammonium ion $NH_4^+$ or a metal ion, such as, for example, an $Na^+$, $Li^+$, $K^+$, $Mg^{2+}$, $Ca^{2+}$, $Cu^{2+}$, $Fe^{2+}$ or $Fe^{3+}$ ion. Mention may in particular be made of the polymers described in U.S. Pat. Nos. 3,734,874, 4,233,196 and 4,304,901, the disclosures of which are specifically incorporated by reference herein;

polyesters containing a fatty chain, polyamides and epoxyester resins;

polyurethane polymers, in particular anionic, cationic, non-ionic or amphoteric polyurethanes, polyurethanes-acrylics, polyurethanes-polyvinylpyrrolidones, polyesters-polyurethanes, polyethers-polyurethanes, polyureas, polyureas-polyurethanes, and their mixtures;

optionally modified polymers of natural origin, such as:

arabic gums, guar gum, xanthan derivatives or karaya gum;

alginates and carrageenates;

glycoaminoglycans, hyaluronic acid and its derivatives;

shellac resin, sandarac gum, dammars, elemis or copals;

resins of the arylsulfonamide-formaldehyde or arylsulfonamide-epoxy type, in particular resins known under the tradenames SANTOLITE MHP® and SANTOLITE MS 80%®); and synthetic aqueous dispersions, such as, for example, dispersions of poly(vinyl acetate), of polyurethane, of acrylic polymers or copolymers and of poly(vinyl acetate) copolymers.

The compounds of formula (I):

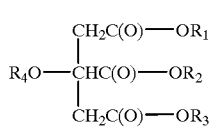

(I)

in which:

$R_1$, $R_2$ and $R_3$ independently represent H or a saturated or unsaturated, linear or branched $C_1$–$C_{30}$ alkyl chain or a saturated or unsaturated cyclic $C_3$–$C_{30}$ alkyl chain, and wherein at least one of $R_1$, $R_2$ and $R_3$ is not a hydrogen atom, and $R_4$ represents a hydrogen atom or an $R'_4$—CO— group in which $R'_4$ represents a $C_1$–$C_8$ alkyl group; are compounds known to persons skilled in the art. Mention may in particular be made of triethyl citrate, tributyl citrate, triethyl acetylcitrate and tri(2-ethylhexyl) acetylcitrate.

The compounds of formula (II) are compounds also well known to persons skilled in the art. Mention may in particular be made of N-ethyl-o,p-toluenesulfonamide (mixture of the ortho and para isomers), which is available commercially, for example from the company Monsanto, under the tradename SANTICIZER 8.

Advantageously, in the combination according to the invention, the film-forming polymer (a), the compound of formula (I) (b), and the compound of formula (II) (c), are present in amounts which satisfy the relationship:

$1 < (a)/[(b)+(c)] < 4$ and more preferably still the relationship:

$1.5 < (a)/[(b)+(c)] < 2.5$

Advantageously, the compound of formula (I) (b) and the compound of formula (II) (c) are present in amounts which satisfy the relationship:

$0.3 < (b)/(c) < 3$ and more preferably still, the relationship:

$0.8 < (b)/(c) < 1.5$

Another subject of the invention is a cosmetic and/or dermatological composition comprising the combination described above in a cosmetically and/or dermatologically acceptable vehicle.

The cosmetic and/or dermatological compositions according to the invention are those relating to making up the eyelashes, eyebrows, hair and nails, that is to say eyeliners, mascaras, gels, creams, lacquers or foams for the hair, nail varnishes, nail care bases and finishing or top-coat make-ups.

In the case where the composition is intended to be applied to the eyelashes, eyebrows and/or hair, the film-forming polymer is used in amounts which make it possible to obtain good adhesion of the composition on the keratinous fibre. In this case, the compositions according to the invention preferably comprise an amount of film-forming polymer ranging from 0.1 to 25% by weight with respect to the total weight of the composition, more preferably from 1 to 10%.

In the case where the composition is intended to be applied to the nails, the film-forming material of the varnish or of the nail care base is preferably present at a concentration ranging from 2 to 40%, more preferably from 5 to 25%, by weight with respect to the total weight of the composition.

Besides the plasticizing agents included in the combination according to the invention (compound of formula (I) and compound of formula (II)), provision may be made for the composition according to the invention to also comprise an additional plasticizing agent used conventionally in cosmetics, such as, for example, tricresyl phosphate, benzyl benzoate, diamyl phthalate, camphor or dibutyl phthalate.

The composition according to the invention can, in addition, comprise at least one coloring agent, such as conventional pigments or dyes.

Pigments are natural or synthetic substances composed of fine particles which, in contrast to dyes, are insoluble in their medium of use, the main function of which is to give a coloring. Different types of pigments are distinguished between: inorganic pigments, metallic pigments, organic pigments, lakes or pearlescent pigments. Lakes are dyes adsorbed on insoluble particles, the combination remaining essentially insoluble in the medium of use. Pearlescent pigments are natural or synthetic substances which scatter and reflect light to give an iridescent or gloss effect.

Mention may be made, among dyes, of natural organic dyes, such as cochineal carmine (Cl 75 470), or synthetic organic dyes, such as haloacid, azo or anthraquinone dyes. Mention may also be made of inorganic dyes, such as copper sulphate.

Mention may be made, among inorganic pigments, of metal oxides, in particular zirconium, cerium, zinc or chromium oxides (Cl 77 288), titanium dioxide (Cl 77 891), black, yellow, red and brown iron oxides (Cl 77 499, Cl 77492 or Cl 77491), manganese violet (Cl 77 742), ultramarine blue (Cl 77 007), iron blue (Cl 77 510), chromium hydrate (Cl 77 289), silver powder or aluminium powder.

Mention may be made, among organic pigments, of carbon black (Cl 77266) or D & C Red 36 (Cl12085).

Lakes are generally composed of metal salts (in particular Al, Zr, Ca or Na) of organic dyes adsorbed on particles, for example of alumina, of barium sulphate, of colophony, and the like. Mention may be made, among lakes, of those known under the names: D & C Red 21 (Cl 45 380), D & C Orange 5 (Cl 45 370), D & C Red 27 (Cl 45 410), D & C Orange 10 (Cl 45425), D & C Red 3 (Cl 45 430), D & C Red 7 (Cl 15 850:1), D & C Red 4 (Cl 15 510), D & C Red 33 (Cl 17 200), D & C Yellow 5 (Cl 19 140), D & C Yellow 6 (Cl 15 985), D & C Green 5 (Cl 61 570), D & C Yellow 10 (Cl 77 002), D & C Green 3 (Cl 42 053), D & C Blue 1 (Cl 42 090).

Mention may be made, among pearlescent pigments, of bismuth oxychloride or mica covered with titanium oxide, with iron oxide or with natural pigments, for example colored titanium dioxide-coated mica.

In the compositions according to the invention, the total amount of coloring agents preferably ranges from approximately 0.01 to approximately 60% by weight with respect to the total weight of the composition, more preferably from approximately 0.05 to approximately 30% by weight, and even more preferably from approximately 0.5 to approximately 5% by weight.

The cosmetic compositions according to the invention can furthermore contain additional fillers usual in cosmetics.

Fillers are natural or synthetic materials, the main function of which is to modify the physicochemical (rheological, mechanical, optical) and/or cosmetic properties of a composition. Fillers are colorless or more or less white in the dry state. They are virtually transparent when dispersed in a binder.

Mention may be made, among fillers, of talc, which is a hydrated magnesium silicate used in the form of particles with dimensions generally of less than 40 μm; talc possesses moisture-absorbing properties and is used especially because of its smooth feel; micas, which are aluminosilicates of varied compositions which are provided in the form of flakes having dimensions preferably from 2 to 200 μm, more preferably from 5 to 70 μm, and a thickness preferably from 0.1 to 5 μm, more preferably from 0.2 to 3 μm; micas can be of natural origin (muscovite, margarite, roscoelite, lepidolite or biotite, for example) or of synthetic origin; they are generally transparent and make it possible to confer a satin appearance on the skin; starch, in particular rice starch; silica; kaolin, which is a hydrated aluminium silicate, which is provided in the form of particles with an isotropic shape having dimensions generally of less than 30 μm and which has good absorption properties with respect to fatty substances; NYLON® (in particular ORGASOL) and polyethylene powders; TEFLON®; boron nitride; copolymer microspheres, such as EXPANCEL® (Nobel Industrie) or POLYTRAP® (Dow Corning), and silicone resin microbeads (TOSPEARLS® from Toshiba, for example); precipitated calcium carbonate, which, in the form of particles with dimensions of less than 10 μm, has a smooth feel and makes it possible to obtain a matte appearance; magnesium carbonate or hydrocarbonate which has in particular perfume-fixing properties; metal soaps derived from organic carboxylic acids preferably having from 8 to 22 carbon atoms, more preferably from 12 to 18 carbon atoms, for example zinc, magnesium or lithium stearate, zinc laurate, magnesium myristate, and the like; these soaps, generally present in the form of particles having dimensions of less than 10 μm, have a smooth feel and facilitate adhesion of the powder to the skin.

According to the type of formulation, the fillers preferably represent from 0.01 to 90% by weight of the composition.

The compositions according to the present invention can in particular be provided in the form of an oil-in-water or water-in-oil emulsion, in the form of a solution in organic or aqueous solvent medium, or in the form of a suspension in organic or aqueous solvent medium, or alternatively in the gel or mousse form. The procedures for the preparation of these different types of composition are well known to the person skilled in the art.

When they are used in the emulsion form, the compositions according to the invention can contain surface-active agents well known in the state of the art. These surfactants preferably constitute from 0.01 to 30% by weight with respect to the total weight of the composition.

A particularly preferred embodiment comprises the preparation of anionic or non-ionic emulsions by using anionic or non-ionic surface-active agents in proportions preferably ranging from 2 to 30% by weight with respect to the total weight of the composition.

Mention may in particular be made, among anionic surface-active agents which can be used alone or as a mixture, of alkali metal salts, ammonium salts, amine salts or aminoalcohol salts of the following compounds:

alkyl sulphates, alkyl ether sulphates, alkylamide sulphates, ether sulphates, alkylaryl polyether sulphates and monoglyceride sulphates, alkylsulphonates, alkylamide sulphonates, alkylarylsulphonates, α-olefin sulphonates and paraffin sulphonates, alkyl sulphosuccinates, alkyl ether sulphosuccinates, and alkylamide sulphosuccinates, alkyl sulphosuccinamates, alkyl sulphoacetates and alkyl polyglycerol carboxylates, alkyl phosphates and alkyl ether phosphates, acylsarcosinates, alkylpolypeptidates, alkylamidopolypeptidates, acylisethionates and alkyllaurates.

The alkyl or acyl radical in all these compounds generally denotes a chain containing from 12 to 18 carbon atoms.

Other anionic surface-active agents that can be used are composed of salts of fatty acids, such as oleic, ricinoleic, palmitic and stearic acids, coconut oil acid or hydrogenated coconut oil acid, and in particular amine salts, such as amine stearates.

Mention may also be made of:

acyllactylates in which the acyl radical comprises from 8 to 20 carbon atoms, polyglycol ether carboxylic acids corresponding to the formula:

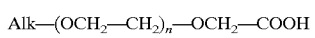

in the acid or salified form, where the substituent Alk corresponds to a linear chain having from 12 to 18 carbon atoms, and where n is an integer ranging from 5 to 15.

Mention may be made, among non-ionic surfactants which can be used alone or as a mixture, of in particular: polyethoxylated, polypropoxylated or polyglycerolated alcohols, alkylphenols and fatty acids with a fatty chain containing from 8 to 18 carbon atoms. Mention may also be made of copolymers of ethylene oxide and of propylene oxide, condensates of ethylene and propylene oxide with fatty alcohols, polyethoxylated fatty amides, polyethoxylated fatty amines, ethanolamides, fatty acid esters of glycol, optionally oxyethylenated fatty acid esters of sorbitan, fatty acid esters of sucrose, fatty acid esters of polyethylene glycol, phosphoric triesters or fatty acid esters of glucose derivatives.

Other compounds which come within this classification and can be used in accordance with the present invention are condensation products of an α-diol, of a monoalcohol, of an alkylphenol, of an amide or of a diglycolamide with glycidol or a glycidol precursor.

The non-ionic surfactants which are preferably used are polyethoxylated and polyglycerolated alcohols, such as polyethoxylated stearyl, cetylstearyl and oleyl alcohols.

The preferentially used anionic surfactants are amine stearates.

The compositions according to the invention can also be provided in the form of a gel, of an aqueous or aqueous/ alcoholic solution of one or a number of water-soluble polymers, such as polyacrylic acid derivatives, or in the form of emulsified gels obtained by dispersion of oils in gels using emulsifiers such as PEMULENS® from the company Goodrich.

The compositions according to the present invention can additionally contain standard ingredients selected from softeners, preservatives, sequestering agents, fragrances, thickeners, cohesion agents or polymers, as well as basifying or acidifying agents, moisturizing agents and water-soluble active principles.

The thickeners which can be used may be natural or synthetic. Mention may be made, among natural thickeners, of gums of various sorts, such as arabic gum, guar gum or locust bean gum. Mention may be made, among synthetic thickeners, of cellulose derivatives, such as hydroxyethyl cellulose or carboxymethyl cellulose, starch derivatives, cellulose ether derivatives possessing quaternary ammonium groups, cationic polysaccharides, salts of acrylic or methacrylic polymers, polyenes or polysiloxanes.

It is also possible to obtain a thickening of the compositions of the invention by mixing polyethylene glycol and polyethylene glycol stearate and/or distearate or with a mixture of phosphoric esters and of fatty amides.

According to the invention, the oily phase can preferably represent from 0.1 to 50% by weight with respect to the total weight of the emulsion. It can be composed of oils and/or of waxes. The waxes and the oils can be of vegetable, animal, mineral or synthetic origin.

Mention may be made, among the vegetable oils, of jojoba oil, olive oil, sweet almond oil, avocado oil, coconut oil, wheatgerm oil, maize oil, palm oil, sesame oil, soybean oil, argan oil, evening primrose oil, borage oil and essential oils.

Mention may in particular be made, among animal oils, of fish oil.

Mention may be made, among mineral oils, of liquid paraffin and of isohexadecane.

Mention may be made, among synthetic oils, of ethyl and isopropyl palmitates, 2-ethylhexyl palmitate, alkyl myristates, such as isopropyl, butyl or cetyl myristate, hexyl stearate, triglycerides of octanoic and decanoic acids, cetyl ricinoleate and stearyl octanoate, silicone oils, perfluorinated oils or fluorinated silicone oils.

The oily phase can moreover contain dyes, sunscreen agents, antioxidants, preservatives and lipophilic active principles.

According to the invention, the anhydrous compositions which can be provided in the solid, pasty or liquid make-up form can contain a binder which preferably represents from 0.01 to 95% by weight with respect to the total weight of the composition.

Mention may in particular be made, among binding agents, of animal, vegetable or synthetic oils or mixtures of oil(s) and wax(es) and in particular mink oil, turtle oil, soybean oil, grape seed oil, sesame oil, maize oil, rapeseed oil, sunflower oil, cottonseed oil, avocado oil, olive oil, castor oil, jojoba oil, groundnut oil, and the like; hydrocarbon oils, such as liquid paraffins, squalane, petrolatum, and the like; esters, such as isopropyl myristate, isopropyl palmitate, butyl stearate, hexyl laurate, isononyl isononanate, 2-ethylhexyl palmitate, 2-hexyldecyl laurate, 2-octyldecyl palmitate, 2-octyidodecyl myristate, di(2-ethylhexyl) succinate, diisostearyl malate, 2-octyldodecyl lactate, glycerol triisostearate, diglyceryl triisostearate, and the like; silicone oils, such as polymethylsiloxanes, polymethylphenylsiloxanes, polysiloxanes modified by fatty acids, polysiloxanes modified by fatty alcohols, polysiloxanes modified by polyoxyalkylenes, fluorinated silicones, and the like; perfluorinated and/or organofluorinated oils; higher fatty acids, such as myristic acid, palmitic acid, stearic acid, behenic acid, oleic acid, linoleic acid, linolenic acid, isostearic acid, and the like; higher fatty alcohols, such as cetanol, stearyl alcohol, oleyl alcohol and the like; the waxes can be selected in particular from carnauba wax, candelilla wax, beeswax, whale wax, lanolins, microcrystalline waxes, and the like.

The binder can additionally contain volatile oils, which will evaporate on contact with the skin but the presence of which in the cosmetic composition is useful because they facilitate spreading of the composition during application to the skin. Such spreading agents, known here as "volatile oils," are generally oils having, at 25° C., a saturated vapor pressure of at least 0.5 millibar (i.e., 50 Pa).

Mention will be made, among the volatile oils which can be present as spreading agents in the compositions of the invention, for example, of silicone oils, such as hexamethyldisiloxane, cyclopentadimethylsiloxane or cyclotetramethylsiloxane, fluorinated oils, such as that sold under the name GALDEN® (Montefluos), or isoparaffin oils, such as those sold under the name ISOPAR® (E, G, L or H; Exxon Chemical).

As mentioned above, the compositions according to the invention can also be provided in the form of an anhydrous or aqueous nail varnish or nail care base.

Advantageously, when the composition is intended to be applied to the nails, it contains a total amount of plasticizing agent (compound of formula (I), compound of formula (II) and optionally at least one other plasticizer) preferably ranging from 2 to 20%, more preferably from 5 to 15%, by weight with respect to the total weight of the composition.

When the compositions are provided in the form of an anhydrous nail varnish or nail care base, the solvent system preferably represents from approximately 55% to approximately 90% by weight with respect to the total weight of the varnish.

This solvent system is composed of a mixture of various volatile organic solvents, such as acetone, ethyl acetate, butyl acetate, 2-methoxyethyl acetate, methyl ethyl ketone, methyl isobutyl ketone, methyl acetate, amyl acetate and isopropyl acetate, or alcohols, such as ethanol or isopropanol.

The solvent system can also comprise a diluent, such as hexane or octane or alternatively an aromatic hydrocarbon, such as toluene or xylene, in a proportion preferably of from 10 to 35% by weight with respect to the total weight of the varnish. The film-forming material of the varnish is preferably present in a concentration ranging from 5 to 20% by weight with respect to the total weight of the varnish.

Mention may in particular be made, among film-forming materials commonly used in nail care base and varnish compositions, of nitrocelluloses of the "RS" or "SS" type and in particular nitrocellulose type ¼"RS", nitrocellulose type ½"RS", nitrocellulose type ½"SS" and nitrocellulose type ¾"RS".

The varnishes according to the invention can also comprise a resin generally present at a concentration ranging from 0 to 15% by weight with respect to the total weight of the varnish.

Mention may in particular be made, among the numerous resins which can be used, of resins of the arylsulphonamide-formaldehyde or arylsulphonamide-epoxy type, in particular the resins known under the trade names SANTOLITE MHP® and SANTOLITE MS 80®.

When the nail varnishes or nail care bases are provided in the aqueous form, they contain a dispersion of a synthetic film-forming substance to which various standard additives can be added, such as a film-forming material, a thickener, a pH regulator, a crosslinking agent, an antifoaming agent, and the like.

It is possible, as a synthetic aqueous dispersion, inter alia, to use dispersions of poly(vinyl acetate), of polyurethane, of acrylic polymers or copolymers and of copolymers of poly (vinyl acetate).

According to the invention, the synthetic aqueous dispersion preferably represents approximately from 10 to 80% by weight of the varnish.

Mention may in particular be made, among the film-forming materials, of water-soluble cellulose derivatives.

The varnishes according to the invention can also comprise a resin generally present at a concentration ranging from 0 to 15% by weight with respect to the total weight of the varnish.

Mention may in particular be made, among the resins which can be used, of resins of the acrylic, styrene, acrylate-styrene and vinyl type.

The anhydrous or aqueous nail varnishes according to the invention can also contain adjuvants commonly used in nail varnishes, such as, for example, U.V. to screening agents.

The invention is illustrated in more detail in the following examples.

EXAMPLE 1: Nail Varnish Composition

A composition according to the invention was prepared comprising:

| | |
|---|---|
| nitrocellulose | 19% |
| N-ethyl-o,p-toluenesulphonamide | 6% |
| tributyl acetylcitrate | 6% |
| pigments | 1% |
| hectorite | 1.2% |
| isopropyl alcohol | 8% |
| ethyl acetate, butyl acetate | q.s. for 100% |

EXAMPLE 2: COMPARATIVE TESTS

Formulae tested:

| | Formula A | Formula B | Formula C |
|---|---|---|---|
| Nitrocellulose | 20% | 20% | 20% |
| N-ethyl-o,p-toluenesulphonamide | 12% | — | 6% |
| Tributyl acetylcitrate | — | 12% | 6% |
| Ethyl acetate/Butyl acetate (50/50) | q.s. for 100% | q.s. for 100% | q.s. for 100% |

A—STUDY OF YELLOWING:

The yellowing after storage for 1 to 4 weeks at 45° C. was evaluated visually. A grade from 0 to 10 was attributed to each sample:
0=no coloration
10=very yellow
The results are given in the table below:

| | Formula A | Formula B | Formula C |
|---|---|---|---|
| 1 week | 1 | 1 | 1 |
| 2 weeks | 2 | 1 | 1 |
| 3 weeks | 3 | 2 | 2 |
| 4 weeks | 4 | 2 | 2 |

It was thus found that the combination of the two plasticizers has very good resistance to yellowing, whereas N-ethyl-o,p-toluenesulphonamide employed alone gave a composition which rapidly yellowed.

B—MEASUREMENT OF THE GLOSS:

Gloss measurements were carried out, using a Micro Tri Gloss Glossmeter sold by the company Byk Gardner, at an angle of 60°.

These measurements were carried out on the formulae A, B and C described above, and on the formulae A', B' and C' which derive from the formulae A, B and C by addition of 1% by weight of red pigment.

The results are given in the table below:

| | Formula A | Formula B | Formula C |
|---|---|---|---|
| Gloss | 80.9 | 69.8 | 80.1 |
| | Formula A' | Formula B' | Formula C' |
| Gloss | 81.7 | 75.1 | 80.3 |

It was found, from these tests, that the mixture of the two plasticizers made it possible to obtain an excellent gloss, whereas tributyl acetylcitrate employed alone only made it possible to obtain an average result.

We claim:

1. A cosmetic composition for forming a film on skin, eyelashes, eyebrows, hair, or nails comprising:

(a) at least one film-forming polymer;

(b) at least one citric acid ester of formula (I):

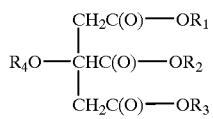

(I)

in which:

$R_1$, $R_2$ and $R_3$ independently represent H or a saturated or unsaturated, linear or branched $C_1$–$C_{30}$ alkyl group, wherein at least one of $R_1$, $R_2$ and $R_3$ is not a hydrogen atom, $R_4$ represents a hydrogen atom or an $R'_4$—CO— group in which R', represents a saturated or unsaturated, linear or branched $C_1$–$C_8$ alkyl group or a saturated or unsaturated cyclic $C_3$–$C_8$ alkyl group;

(c) at least one compound of formula (II):

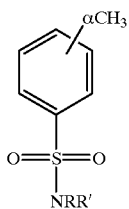

(II)

in which:
α represents an ortho or pare position of the phenyl group, and

R and R' independently represent a hydrogen atom or a saturated or unsaturated, linear or branched $C_1$–$C_6$ alkyl group or a saturated or unsaturated cyclic $C_3$–$C_6$ alkyl group, and (d) at least one additional cosmetic ingredient selected from coloring agents, fillers, preservatives, fragrances, thickeners, waxes, oils, sunscreen agents and antioxidants, wherein the total amount of components (b)+(c) is present in a concentration of at least 2% by weight relative to the total weight of the cosmetic composition.

2. A cosmetic composition according to claim 1, wherein said at least one citric acid ester of formula (I) is selected from tributyl-acetylcitrate triethyl citrate, tributyl citrate, triethyl acetylcitrate and tri(2-ethylhexyl) acetylcitrate.

3. A cosmetic composition according to claim 1, wherein said at least one compound of formula (II) is N-ethyl-o,p-toluenesulphonamide.

4. A cosmetic composition according to claim 1, wherein components (a), (b), and (c) are present in weight percent amounts that satisfy the relationship.

$$1<(a)/[(b)+(c)]<4$$

5. A cosmetic composition according to claim 4, wherein components (a), (b), and (c) are present in weight percent amounts that satisfy the relationship.

$$1.5<(a)/[(b)+(c)]<2.5$$

6. A cosmetic composition according to claim 1, wherein components (b) and (c) are present in weight percent amounts that satisfy the relationship.

$$0.3<(b)/(c)<3$$

7. A cosmetic composition according to claim 6, wherein components (b) and (c) are present in weight percent amounts that satisfy the relationship.

$$0.8<(b)/(c)<1.5$$

8. A cosmetic composition according to claim 1, wherein said cosmetic and/or dermatological composition is a make-up composition for eyelashes, eyebrows, hair and/or nails.

9. A cosmetic composition according to claim 8, wherein said cosmetic composition is a make-up composition for eyelashes, eyebrows, and/or hair comprising said at least one film-forming polymer in a concentration ranging from 0.1 to 25% by weight relative to the total weight of the cosmetic composition.

10. A cosmetic composition according to claim 9, wherein said cosmetic composition comprises said at least one film-forming polymer in a concentration ranging from 1 to 10% by weight relative to the total weight of the cosmetic composition.

11. A cosmetic composition according to claim 8, wherein said cosmetic composition is a make-up composition for nails comprising said at least one film-forming polymer in a concentration ranging from 2 to 40%, by weight relative to the total weight of the cosmetic composition.

12. A cosmetic composition according to claim 11, wherein said cosmetic composition comprises said at least one film-forming polymer in a concentration ranging from 5 to 25%, by weight relative to the total weight of the cosmetic composition.

13. A cosmetic composition according to claim 1, wherein said at least one additional cosmetic ingredient is selected from coloring agents present in a concentration ranging from 0.01 to 60% by weight relative to the total weight of the cosmetic composition.

14. A cosmetic composition according to claim 13, wherein said coloring agents are present in a concentration ranging from 0.05 to 30% by weight relative to the total weight of the cosmetic composition.

15. A cosmetic composition according to claim 14, wherein said coloring agents are present in a concentration ranging from 0.5 to 5% by weight relative to the total weight of the cosmetic composition.

16. A cosmetic composition according to claim 1, wherein said at least one additional cosmetic ingredient is selected from fillers present in a concentration ranging from 0.01 to 90% by weight, relative to the total weight of the cosmetic composition.

17. A cosmetic composition according to claim 1, wherein said cosmetic composition further comprises at least one surface-active agent.

18. A cosmetic and/or dermatological composition according to claim 17, wherein said at least one surface-active agent is present in a concentration ranging form 0.01 to 30% by weight, relative to the total weight of the cosmetic and/or dermatological composition.

19. A cosmetic composition according to claim 17, wherein said at least one surface-active agent is selected from anionic and non-ionic surface-active agents.

20. A cosmetic composition according to claim 18, wherein said at least one surface-active agent is present in a concentration ranging from 2 to 30% by weight, relative to the total weight of the cosmetic and/or dermatological composition.

21. A cosmetic composition according to claim 8, wherein said cosmetic and/or dermatological composition is in the form of an anhydrous nail varnish or nail care base.

22. A cosmetic composition according to claim 8, wherein said cosmetic and/or dermatological composition is in the form of an aqueous nail varnish or nail care base.

23. A cosmetic composition according to claim 8, wherein said cosmetic and/or dermatological composition is a make-up composition for nails wherein the total amount of components (b)+(c) is present in a plasticizing concentration ranging from 2 to 20% by weight, relative to the total weight of the cosmetic and/or dermatological composition.

24. A cosmetic composition according to claim 23, wherein said total amount of components (b)+(c) is present in a plasticizing concentration ranging from 5 to 15% by weight, relative to the total weight of the cosmetic and/or dermatological composition. plasticizing agent) is present in a plasticizing concentration ranging from 2 to 20% by weight, relative to the total weight of the cosmetic and/or dermatological composition.

25. A cosmetic composition according to claim 1, wherein said cosmetic composition further comprises at least one additional plasticizing agent.

26. A cosmetic composition according to claim 25, wherein the total amount of components (b)+(c)+said at least one additional plasticizing agent is present in a plasticizing concentration ranging from 2 to 20% by weight, relative to the total weight of the cosmetic composition.

27. A cosmetic composition according to claim 26, wherein said total amount of components (b)+(c)+at least additional plasticizing agent is present in a plasticizing concentration ranging from 5 to 15% by weight, relative to the total weight of the cosmetic composition.

* * * * *

UNITED STATES PATENT AND TRADEMARK OFFICE
CERTIFICATE OF CORRECTION

PATENT NO. : 6,110,447
DATED : August 29, 2000
INVENTOR(S) : Roland RAMIN et al.

It is certified that error appears in the above-identified patent and that said Letters Patent is hereby corrected as shown below:

On the title page, line 2, after "POLYMER", insert --,--.

Inventors, front page, line 3, before "Bridge", insert --Building--.

ABSTRACT, front page, line 20, delete "and/or dermatological".

Claim 1, col. 10, line 65, change "R'," to --$R'_4$--; and col. 11, line 15, change "pare" to --para--.

Claim 2, col. 11, line 30, after "-acetylcitrate", insert --,--.

Claim 8, col. 11, line 58, delete "and/or dermatological".

Claim 18, col. 12, line 35, delete "and/or dermatological"; and col. 12, line 39, delete "and/or dematological".

Claim 20, col. 12, line 46, delete "and/or dermatological".

Claim 21, col. 12, line 49, delete "and/or dermatological".

Claim 22, col. 12, line 52, delete "and/or dermatological".

Claim 23, col. 12, line 55, delete "and/or dermatological"; and col. 12, line 59, delete "and/or dermatological".

UNITED STATES PATENT AND TRADEMARK OFFICE
CERTIFICATE OF CORRECTION

PATENT NO. : 6,110,447
DATED : August 29, 2000
INVENTOR(S) : Rolamd RAMIN et al.

It is certified that error appears in the above-identified patent and that said Letters Patent is hereby corrected as shown below:

Claim 24, col. 12, line 63, delete "and/or";

col. 23, line 64, delete "dermatological";

and "plasticizing agent is present in"; and col. 12, lines 65-67, delete in its entirety.

Signed and Sealed this

Twenty-ninth Day of May, 2001

*Attest:*

NICHOLAS P. GODICI

*Attesting Officer*   *Acting Director of the United States Patent and Trademark Office*